United States Patent [19]

Botannet et al.

[11] Patent Number: 5,013,855
[45] Date of Patent: May 7, 1991

[54] PROCESS FOR THE PREPARATION OF AROMATIC ETHERS

[75] Inventors: Bernard Botannet, Vienne; Isidore Le Fur, Thiais; Viviane Massonneau; Michel Mulhauser, both of Ecully, all of France

[73] Assignee: Rhone-Poulenc Sante, Antony, France

[21] Appl. No.: 526,703

[22] Filed: May 22, 1990

[30] Foreign Application Priority Data

May 23, 1989 [FR] France .................................. 89 06701

[51] Int. Cl.$^5$ .................. C07D 301/02; C07D 303/23
[52] U.S. Cl. ...................................... 549/539; 549/561
[58] Field of Search ............................... 549/539, 561

[56] References Cited

U.S. PATENT DOCUMENTS 3,994,878 11/1976 Partridge, Jr. et al. ............ 549/561

*Primary Examiner*—Frederick E. Waddell
*Assistant Examiner*—Ba K. Triny
*Attorney, Agent, or Firm*—Morgan & Finnegan

[57] ABSTRACT

A process for the preparation of an aromatic ether of general formula:

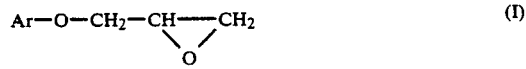

by the action of 3-chloro-1,2-propanediol sulfate on a phenol of general formula:

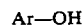

Ar—OH in the presence of an inorganic base.

Use of a product obtained according to the process for the preparation of adrenergic β-blockers.

4 Claims, No Drawings

PROCESS FOR THE PREPARATION OF AROMATIC ETHERS

The present invention relates to a process for preparation of aromatic ethers of general formula:

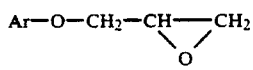  (I)

in which Ar denotes an aromatic radical or a heterocyclic aromatic radical, optionally substituted.

The products of general formula (I) are in particular intermediates for the preparation of adrenergic β-blockers which are characterized by the presence of a 3-alkylamino-2-hydoxypropoxy chain, such as acebutolol, atenolol, propranolol, metoprolol, timolol, nadolol or pindolol.

Adrenergic β-blockers are generally obtained by the action of a primary amine on the epoxide of general formula (I), which is itself obtained by the action of epichlorohydrin on a phenol of general formula:

 Ar-OH  (II)

in which Ar is defined as above. However, an excess of epichlorohydrin must be employed to limit the formation of secondary products such as Ar-O-CH$_2$-CH(OH)-CH$_2$-O-Ar. Despite the excess of epichlorohydrin the formation of secondary products entails a considerable decrease in the yield of product of general formula (I) and a necessary purification of the product of general formula (I) or of the products obtained by using the product of general formula (I).

It has now been found, and this is what forms the subject of the present invention, that aromatic ethers of general formula (I) can be obtained in good yields, without formation of secondary products, by the action of a 3-halo-1,2-propanediol sulfate of general formula:

  (III)

in which X denotes a halogen (chlorine, bromine) atom on a phenol of general formula (II) in which Ar is defined as above, and passing intermediately and successively via the products of general formula:

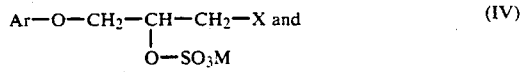  (IV)

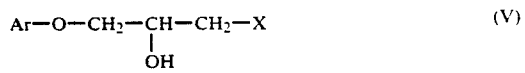  (V)

in which Ar and X are defined as above and M denotes a hydrogen atom or an alkali metal atom or an ammonium ion, which it is unnecessary to isolate.

The condensation of the cyclic sulfate of general formula (III) with the phenol of general formula (II) is generally carried out in water or in an organic solvent or in a hydroorganic medium at a temperature of between 0 and 80° C. in the presence of a base chosen from alkali metal hydroxides (soda), alkali metal carbonates or bicarbonates (sodium carbonate), aqueous ammonia or quaternary ammonium hydroxides (tetrabutylammonium hydroxide).

Organic solvents which may be employed are nitriles (acetonitrile), ketones (acetone), alcohols (ethanol), esters (ethyl acetate), amides (dimethylformamide) or halogenated aliphatic hydrocarbons (methylene chloride).

A slight molar excess, preferably close to 10%, of cyclic sulfate of general formula (III) is generally employed in relation to the phenol of general formula (II).

When a phenol of general formula (II) bearing substituents which can react with the cyclic sulfate of general formula (III) is employed, it may be advantageous to protect them by suitable protective groups which can subsequently be removed without affecting the remainder of the molecule.

The product of general formula (I) is isolated from the reaction mixture by the application of the usual techniques.

The 3-halo-1,2-propanediol sulfate of general formula (III) can be obtained by oxidation of the corresponding sulfite.

The oxidation is generally carried out by the use of a hypohalite (alkali or alkaline-earth metal hypochlorite or hypobromite), preferably sodium, potassium or calcium hypochlorite, in the presence of a catalytic quantity of a ruthenium derivative, preferably chosen from ruthenium(IV) oxide (RuO$_2$) and ruthenium chloride (RuCl$_3$).

The process may be carried out in an aqueous or 2-phase hydroorganic medium.

When the process is carried out in a 2-phase hydroorganic medium, the solvent is generally chosen from optionally halogenated aliphatic or cycloaliphatic hydrocarbons such as hexane, cyclohexane, methylene chloride, chloroform, carbon tetrachloride or dichloroethane, and esters such as methyl acetate or ethyl acetate.

A catalytic quantity of ruthenium derivative of between 10$^{-6}$ and 10$^{-1}$ mole per mole of cyclic sulfite is generally employed.

The cyclic sulfate of general formula (III) is isolated from the reaction mixture according to the usual techniques.

The cyclic 3-halo-1,2-propanediol sulfite can be prepared according to known methods and in particular according to the process described by D. S. Breslow and H. Solnik, "The Chemistry of Heterocyclic Compounds - Multi-Sulphur and Sulphur and Oxygen 5- and 6-Membered Heterocycles", 1966, Part I, p. 1 and Part II, p. 663 or by H. F. Van Woerden, Chem. Rev., 63, 557 (1963).

Adrenergic β-blockers containing a 3-alkylamino-2-hydroxypropoxy chain can be obtained according to known methods by the action of a primary amine on the product of general formula (I).

Adrenergic β-blockers containing a 3-alkylamino-2-hydroxypropoxy chain can also be obtained by the action of a primary amine on the product of general formula (IV) followed by the replacement of the sulfate (SO$_4$H) residue by a hydroxyl radical in acidic or basic medium.

The product of general formula (IV), which is a new product forming another subject of the present invention, can be obtained by controlling the reaction of condensation of the cyclic sulfate of general formula (III) with the phenol of general formula (II). When all the cyclic sulfate has been consumed the reaction mixture is acidified and the product of general formula (IV) is isolated.

The following example, given without any limitation being implied, illustrates the present invention.

EXAMPLE

2-Acetyl-4-butyramidophenol (2.21 g, 10 mmol), 3-chloro-1,2-propanediol sulfate (2 g, 11.5 mmol) and acetonitrile (30 cc) are introduced into a reactor fitted with a stirrer. Sodium hydroxide (0.5 g, 15 mmol) dissolved in water (2.5 cc) is then added.

Stirring is applied for 5 hours at a temperature near 20° C. until a homogeneous mixture is obtained. Heating to 50° C. is then applied for 25 minutes. The precipitate which appears is separated by filtration. Sodium hydroxide (0.9 g) in solution in water (1.5 cc) is then added. After 10 minutes, stirring, the precipitate formed is separated off by filtration. The solution obtained is concentrated under reduced pressure. 1-(2-Acetyl-4-butyramidophenoxy)-2,3- o epoxypropane (2.5 g) is thus obtained, its characteristics being identical with those of an authentic sample.

The yield is close to 90%.

3-Chloro-1,2-propanediol sulfate can be prepared in the following manner:

3-Chloro-1,2-propanediol sulfite (4.96 g, 0.003 mol) and water (25 cc) are introduced into a 250-cc round bottom flask. After cooling to 0° C., an aqueous solution (22.5 cc) of sodium hypochlorite at a concentration of 2 moles per liter (i.e. 0.045 mol) containing ruthenium-(IV) oxide dihydrate (4.5 mg, $0.027 \times 10^{-3}$ mole) is added with stirring.

Stirring is continued for 5 minutes at 2° C. The reaction mixture is extracted with dichloromethane ($2 \times 20$ cc). The organic phase is treated with isopropanol (0.5 cc) and is then washed with water (15 cc). After drying of the organic phase and concentration under reduced pressure (2 m Hg; 0.47 kPa), 3-chloro-1,2-propanediol sulfate (3.95 g) is obtained in the form of a colourless liquid.

The yield is 76.4%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

We claim:

1. A process for the preparation of aromatic ethers of general formula:

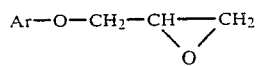

in which Ar denotes an aromatic radical or a heterocyclic aromatic radical, optionally substituted, in which a 3-halo-1,2-propanediol sulfate of general formula:

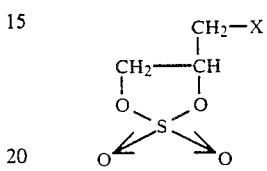

in which X denotes a halogen atom chosen from chlorine and bromine, is reacted with a phenol of general formula:

in which Ar is defined as above, passing intermediately via the products of general formula:

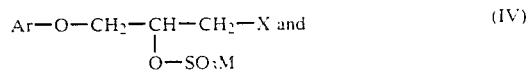

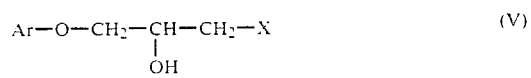

in which Ar and X are defined as above and M denotes a hydrogen atom or an alkali metal atom or an ammonium ion, which it is unnecessary to isolate, the operation being carried out in water or in an organic solvent or in a hydroorganic medium in the presence of a base.

2. The process according to claim 1, wherein the organic solvent is chosen from nitriles, ketones, alcohols, esters, amides and halogenated aliphatic hydrocarbons.

3. The process according to claims 1 wherein the base is chosen from alkali or alkaline-earth metal hydroxides or carbonates or bicarbonates, aqueous ammonia and quaternary ammonium hydroxides.

4. The process according to claim 1 which is carried out at a temperature of between 0 and 80° C.

* * * * *